(12) United States Patent
Taoufik et al.

(10) Patent No.: US 8,993,823 B2
(45) Date of Patent: Mar. 31, 2015

(54) OLEFIN METATHESIS PROCESS USING A CATALYST CONTAINING TUNGSTEN FLUORINE BONDS

(71) Applicant: UOP LLC, Des Plaines, IL (US)

(72) Inventors: Mostafa Taoufik, Villeurbanne (FR); Etienne Mazoyer, Heemstede (NL); Christopher P. Nicholas, Evanston, IL (US); Jean-Marie Basset, Caluire (FR)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/314,512

(22) Filed: Jun. 25, 2014

(65) Prior Publication Data

US 2014/0357922 A1 Dec. 4, 2014

Related U.S. Application Data

(63) Continuation-in-part of application No. 13/156,918, filed on Jun. 9, 2011, now abandoned.

(51) Int. Cl.
*C07C 6/04* (2006.01)

(52) U.S. Cl.
CPC ............... *C07C 6/04* (2013.01); *C07C 2523/30* (2013.01); *C07C 2527/132* (2013.01); *C07C 2521/08* (2013.01); *C07C 2531/22* (2013.01)

USPC ........... 585/643; 502/311; 502/353; 502/152; 502/228; 585/646; 585/647; 585/645

(58) Field of Classification Search
USPC .......... 502/311, 353, 152, 228; 585/646, 647, 585/645

See application file for complete search history.

(56) References Cited

U.S. PATENT DOCUMENTS 5,905,055 A * 5/1999 Verdonck et al. ............. 502/311
2012/0316057 A1* 12/2012 Taoufik et al. ................ 502/155

* cited by examiner

*Primary Examiner* — In Suk Bullock
*Assistant Examiner* — Sharon Pregler

(57) ABSTRACT

A process for the metathesis of olefins has been developed. The process comprises contacting a hydrocarbon feedstock with a catalyst at metathesis conditions. The catalyst comprises a tungsten compound, which contains at least one tungsten-fluoro bond, dispersed or grafted onto a support. A specific example of the catalyst is the compound WOF$(CH_2CMe_3)_3$ grafted onto a silica support. The feedstock comprises a first and a second olefin wherein the second olefin has a carbon number of at least two greater than the first olefin and the product is an olefin with a carbon number intermediate between the first and second olefin. Specifically the process produces propylene from ethylene and butylene.

19 Claims, No Drawings

OLEFIN METATHESIS PROCESS USING A CATALYST CONTAINING TUNGSTEN FLUORINE BONDS

CROSS-REFERENCE TO RELATED APPLICATION

This application is a Continuation-In-Part of copending application Ser. No. 13/156,918 filed Jun. 9, 2011, the contents of which are hereby incorporated by reference in its entirety.

FIELD OF THE INVENTION

This invention relates to an olefin metathesis process using a catalyst containing a tungsten fluorine bond. Specifically the process relates to the production of propylene from ethylene and butylene.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very compound combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. No. 5,026,935 and U.S. Pat. No. 5,026,936. The cracking of olefins in hydrocarbon feedstocks, to produce these lighter olefins from $C_4$ mixtures obtained in refineries and steam cracking units, is described in U.S. Pat. No. 6,858,133; U.S. Pat. No. 7,087,155; and U.S. Pat. No. 7,375,257. U.S. Pat. No. 7,074,976 discloses an olefin metathesis process comprising passing butene and ethylene over a catalyst comprising tungsten halide on a silica support to form propylene at low temperatures. U.S. Pat. No. 5,905,055 discloses a metathesis catalyst containing tungsten, a halide, specifically chloride and a modified support containing niobium.

Olefin metathesis catalysts known in the art include those with tungsten-halide bonds such as $WCl_6$ dispersed upon a support. However, fluorine is distinctly different from other halides in structure and properties based upon on the known reaction chemistry of fluorine with other compounds. The review by Keith Fagnou and Mark Lautens in ANGEW. CHEM. INT. ED. 2002, 41, 26-47, entitled "Halide Effects in Transition Metal Catalysis," within the review section "4.1.3 Transition Metal Fluoride Catalysts," subsection "4.1.3.1. Special Properties of the Fluoride Ligand and Fluorine-metal Complexes," reads:

Transition metal fluoro compounds exhibit interesting properties as a result of the fluoride ligand. Experimental evidence indicates that the fluoride ligand confers substantially different properties to the complex compared to the other halide ions. This difference in reactivity has prompted reviews of the chemistry of these complexes and their application in asymmetric catalysis.

Similarly, it is known that fluoride often has different effects as compared to chloride, bromide and iodide, and in the field of olefin metathesis, the classic series of papers on the mechanism of the olefin metathesis reaction by Dias ("Well-Defined Ruthenium Olefin Metathesis Catalysts: Mechanism and Activity", J. AM. CHEM. SOC. 1997, 119, 3887-3897) and Sanford ("Mechanism and Activity of Ruthenium Olefin Metathesis Catalysts", J. AM. CHEM. SOC. 2001, 123, 6543-6554) do not consider using fluoride as a ligand. Furthermore, the reference by Straub, ADVANCED SYNTHESIS & CATALYSIS (Olefin Metathesis) Volume 349, Issue 1-2, pages 204-214, Jan. 8, 2007 on page 211) states:

Fluoride ligands interact strongly with ruthenium d-orbitals. Anti-bonding orbital interactions (see FIG. 4) are the basis for switching between carbene ligand orientations. In difluoride model complexes, the carbene ligand is predicted to strongly prefer an inactive conformation. This effect of fluoride ligands is even larger than that of the electropositive, but large, iodide in diiodide complexes. The previously expected catalyst activity row $F_2(L)Ru=CH_2>Cl_2(L)Ru=CH_2>Br_2(L)Ru=CH_2>I_2(L)Ru=CH_2$ thus has to be revised to $Cl_2(L)Ru=CH_2>Br_2(L)Ru=CH_2 \geq I_2(L)Ru=CH_2 \geq F_2(L)Ru=CH_2$. Chloride appears to be the best compromise of small electron-donating character and diffuse orbital shape and thus teaches away from the use of fluoride as a ligand on an olefin metathesis catalyst metal center.

Compounds containing other halogens with the same formula form different structures due to the change in the anion/cation radius ratios. Fluoride ions are the smallest and least polarizable of all the anions and fluorides frequently adopt 3D "ionic" structures. This is contrasted with chlorides, bromides and iodides which are larger and more polarizable and frequently adopt mutually similar layer-lattices or chain structures. One has not chosen fluorine as a halide in a catalyst for the metathesis of olefins because it is very well recognized in the art that fluoride possesses very different properties than other halides. In addition, metathesis reactions have been known in the art for a long time and are well studied, yet there is no example of a tungsten-metal compound characterized by having at least one tungsten-fluorine bond which is active for olefin metathesis, much less one which is active once dispersed on a support.

Steam cracking, whether or not combined with conventional metathesis and/or olefin cracking steps, does not yield sufficient propylene to satisfy worldwide demand. Other significant sources of propylene are therefore required. These sources include by-products of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ by-product stream of FCC may be purified in propylene to polymer grade specifications by the separation of $C_4$ hydrocarbons, propane, ethane, and other compounds.

Much of the current propylene production is therefore not "on purpose," but as a by-product of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978, 150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

This invention relates to a process for the metathesis of olefins using a catalyst comprising a tungsten compound having at least one tungsten-fluorine bond. Accordingly, one embodiment comprises an olefin metathesis process comprising contacting a hydrocarbon feedstock with a catalyst at metathesis conditions to produce an olefin product, wherein the hydrocarbon feedstock comprises olefins including a first olefin and a second olefin having a carbon number of at least two greater than that of the first olefin, to produce a third olefin having an intermediate carbon number and the catalyst comprises a tungsten metal compound characterized in that it contains at least one tungsten-fluorine bond, the compound dispersed on a refractory oxide support wherein the compound is chemically bonded to the support. The catalyst does not comprise a promoter comprising a niobium compound.

In a specific embodiment, the first olefin is ethylene, the second olefin is butylene and the third olefin is propylene.

In a specific embodiment, the tungsten compound is selected from the group consisting of $WOF(CH_2CMe_3)_3$, $W(NR')F(CH_2CMe_3)_3$, and mixtures thereof and wherein R' is selected from the group consisting of H, phenyl, 2,6-dimethylphenyl and methyl and the support is silica.

In another embodiment, the hydrocarbon feedstock is contacted with the catalyst at a temperature from about 75° C. (167° F.) to about 400° C. (752° F.), an absolute pressure from about 50 kPa (7.3 psi) to about 3,500 kPa (508 psi), and a weight hourly space velocity from about 1 to about 100 $hr^{-1}$.

These and other objects, embodiments and details of this invention will become apparent after a detailed description of the invention.

DETAILED DESCRIPTION OF THE INVENTION

One necessary component of the present invention is a catalyst comprising a tungsten metal compound having at least one tungsten-fluorine bond which is dispersed on a refractory oxide support and the compound is chemically bonded to the support. Olefin metathesis catalysts known in the art include those with tungsten-halide bonds such as $WCl_6$ dispersed upon a support. However, fluorine is distinctly different from other halides in structure and properties based upon on the known reaction chemistry of fluorine with other compounds. The review by Keith Fagnou and Mark Lautens in ANGEW. CHEM. INT. ED. 2002, 41, 26-47, entitled "Halide Effects in Transition Metal Catalysis," within the review section "4.1.3 Transition Metal Fluoride Catalysts," subsection "4.1.3.1. Special Properties of the Fluoride Ligand and Fluorine-metal Complexes," reads:

> Transition metal fluoro compounds exhibit interesting properties as a result of the fluoride ligand. Experimental evidence indicates that the fluoride ligand confers substantially different properties to the complex compared to the other halide ions. This difference in reactivity has prompted reviews of the chemistry of these complexes and their application in asymmetric catalysis.

Similarly, it is known that fluoride often has different effects as compared to chloride, bromide and iodide, and in the field of olefin metathesis, the classic series of papers on the mechanism of the olefin metathesis reaction by Dias ("Well-Defined Ruthenium Olefin Metathesis Catalysts: Mechanism and Activity", J. AM. CHEM. SOC. 1997, 119, 3887-3897) and Sanford ("Mechanism and Activity of Ruthenium Olefin Metathesis Catalysts", J. AM. CHEM. SOC. 2001, 123, 6543-6554) do not consider using fluoride as a ligand. Furthermore, the reference by Straub, ADVANCED SYNTHESIS & CATALYSIS (Olefin Metathesis) Volume 349, Issue 1-2, pages 204-214, Jan. 8, 2007 on page 211) states:

> Fluoride ligands interact strongly with ruthenium d-orbitals. Anti-bonding orbital interactions (see FIG. 4) are the basis for switching between carbene ligand orientations. In difluoride model complexes, the carbene ligand is predicted to strongly prefer an inactive conformation. This effect of fluoride ligands is even larger than that of the electropositive, but large, iodide in diiodide complexes. The previously expected catalyst activity row $F_2(L)Ru=CH_2 > Cl_2(L)Ru=CH_2 > Br_2(L)Ru=CH_2 > I_2(L)Ru=CH_2$ thus has to be revised to $Cl_2(L)Ru=CH_2 > Br_2(L)Ru=CH_2 \geq I_2(L)Ru=CH_2 \geq F_2(L)$ Ru=CH$_2$. Chloride appears to be the best compromise of small electron-donating character and diffuse orbital shape and thus teaches away from the use of fluoride as a ligand on an olefin metathesis catalyst metal center.

Compounds containing other halogens with the same formula form different structures due to the change in the anion/cation radius ratios. Fluoride ions are the smallest and least polarizable of all the anions and fluorides frequently adopt 3D "ionic" structures. This is contrasted with chlorides, bromides and iodides which are larger and more polarizable and frequently adopt mutually similar layer-lattices or chain structures. One has not chosen fluorine as a halide in a catalyst for the metathesis of olefins because it is very well recognized in the art that fluoride possesses very different properties than other halides. In addition, metathesis reactions have been known in the art for a long time and are well studied, yet there is no example of a tungsten-metal compound characterized by having at least one tungsten-fluorine bond which is active for olefin metathesis, much less one which is active once dispersed on a support.

The tungsten metal compound has the empirical formula of: WR$_4$F, WOFR$_3$ or W(NR')FR$_3$, wherein R is an organic group which does not have any hydrogen atoms beta to the tungsten, non-limiting examples of which are neopentyl (—CH$_2$CMe$_3$); methyl, 2,2-diethylpropyl (—CH$_2$C(CH$_2$CH$_3$)$_2$Me), and 2,2-diethylbutyl (—CH$_2$C(CH$_2$CH$_3$)$_2$CH$_2$CH$_3$). Preferably, the number of C atoms in each R group is less than 12. R' is an organic group such as but not limited to H, phenyl, 2,6-dimethylphenyl and methyl. The oxo compound can be synthesized by first reacting O=WCl$_4$ with an alkylating agent such as RMgCl, RLi, RNa or RK to give O=WR$_3$Cl which is then reacted with a fluorinating agent such as AgBF$_4$, HF or NaF to form the O=WR$_3$F compound. The reaction product is treated with a base to remove BF$_3$ impurities, such as but not limited to NR"$_3$ wherein non-limiting examples of R" include H, methyl, ethyl, and phenyl. The overall process can be summarized as follows wherein R is neopentyl and R" is ethyl.

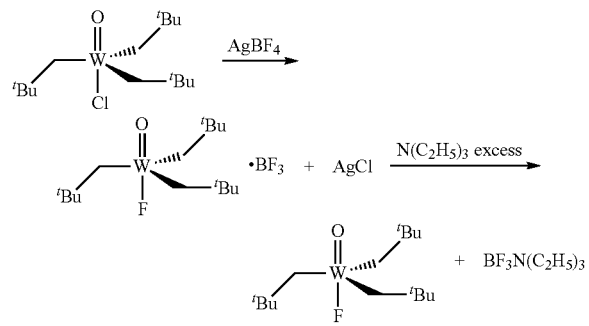

An alternate way to synthesize the oxo tungsten fluoro compound is to react (O=W—O—W=O)R$_6$ with a fluorinating agent (same as above) to produce O=WR$_3$F. Synthesis of (O=W—O—W=O)R$_6$ is described in J. AMER. CHEM. SOC., 1983, vol. 105, 7176-7 which is incorporated by reference in its entirety.

To synthesize the imido compound, often the starting O=WCl$_4$ compound is reacted with R' isocyanate, to yield CO$_2$ and R'N=WCl$_4$ followed by alkylation and fluorination as above. An example of this synthesis is diagrammatically shown below.

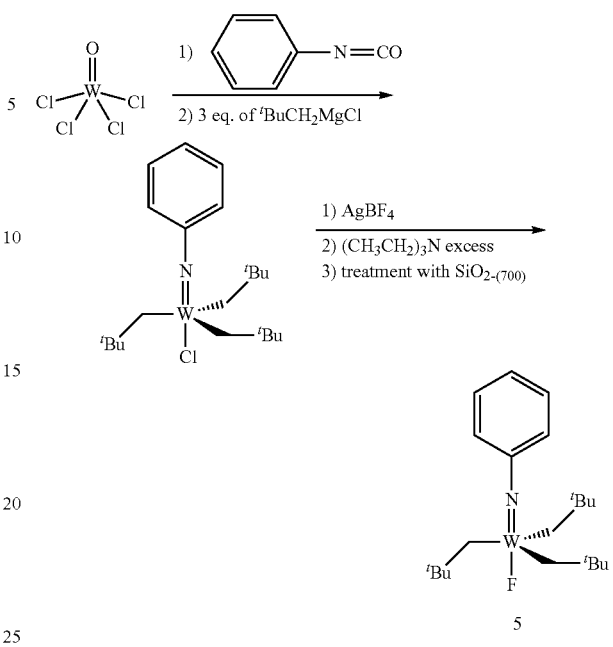

Alternatively, NH$_3$ can be used in place of R' isocyanate to yield HN=WCl$_4$ and H$_2$O. As shown in the above equation, if all the boron is not removed, it can be removed by treatment with silica.

Having obtained the tungsten-fluorine bond containing compound, it is now dispersed or grafted onto an inorganic refractory support. Suitable inorganic refractory supports which can used include, but are not limited to, silica, aluminas, silica-alumina, zirconia, titania, etc. with silica being preferred. Mixtures of refractory oxides can also be used and fall within the bounds of the invention. The support generally has a surface area from about 50 to 1000 m$^2$/g, and preferably from about 80 to about 500 m$^2$/g. It should be pointed out that silica-alumina is not a physical mixture of silica and alumina but means an acidic and amorphous material that has been cogelled or coprecipitated. This term is well known in the art, see e.g., U.S. Pat. No. 3,909,450, U.S. Pat. No. 3,274,124 and U.S. Pat. No. 4,988,659, all of which are incorporated by reference in their entirety. Additionally, naturally occurring silica-aluminas such as attapulgite clay, montmorillonite clay or kieselguhr are within the definition of silica aluminas.

Although the supports can be used as powders, it is preferred to form the powder into shaped articles. Examples of shaped articles include but are not limited to spheres, pills, extrudates, irregularly shaped particles and tablets. Methods of forming these various articles are well known in the art. The support can also be in the form of a layer on an inert core such as described in U.S. Pat. No. 6,177,381 which is incorporated by reference in its entirety.

Spherical particles may be formed, for example, from the preferred alumina by: (1) converting the alumina powder into an alumina sol by reaction with a suitable peptizing acid and water and thereafter dropping a mixture of the resulting sol and a gelling agent into an oil bath to form spherical particles of an alumina gel which are easily converted to a gamma-alumina support by known methods; (2) forming an extrudate from the powder by established methods and thereafter rolling the extrudate particles on a spinning disk until spherical particles are formed which can then be dried and calcined to form the desired particles of spherical support; and (3) wetting the powder with a suitable peptizing agent and thereafter rolling the particles of the powder into spherical masses of the desired size.

Instead of peptizing an alumina powder, spheres can be prepared as described in U.S. Pat. No. 2,620,314 which is incorporated by reference in its entirety. The first step in this method involves forming an aluminum hydrosol by any of the techniques taught in the art and preferably by reacting aluminum metal with hydrochloric acid. The resultant hydrosol is combined with a suitable gelling agent such as hexamethylene tetraamine (HMT). The resultant mixture is dropped into an oil bath which is maintained at a temperature of about 90° to about 100° C. The droplets of the mixture remain in the oil bath until they set and form hydrogel spheres. Next the spheres are continuously withdrawn from the oil bath and treated with an ammoniacal solution at a temperature of about 80° to about 95° C. for a time of about 2 to about 2.5 hours. After treatment with the ammoniacal solution, the spheres are dried at a temperature of about 80° to about 150° C. and then calcined at a temperature of about 400° to about 700° C. for a time of about 1 to about 24 hours.

Extrudates are prepared by mixing the inorganic hydroxide or oxide with water and suitable peptizing agents such as nitric acid, acetic acid, etc. until an extrudable dough is formed. The resulting dough is then extruded through a suitably sized die to form extrudate particles. The extrudate particles are dried at a temperature of about 150° to about 200° C. and then calcined at a temperature of about 450° to 800° C. for a period of about 0.5 to about 10 hours to effect the preferred form of the refractory inorganic oxide.

A preferred support is silica with amorphous silica being one type of silica. Examples include Davisil®646, Davisil®636 (W.R. Grace & Co., Columbia, Md.) and other precipitated silicas. Regardless of the source, the silica will have a surface area, either as received or after an optional acid washing step in the catalyst preparation procedure, of at least about 50 $m^2/g$ and preferably from about 80 to about 500 $m^2/g$, and most preferably from about 400 to about 500 $m^2/g$. Another form of silica which can be used is any of the crystalline mesoporous silicas which are defined to be virtually pure silica. These include materials such as MCM-41 and SBA-15. Additional forms of silica are zeolites which are defined to be virtually pure silica. Zeolites are crystalline aluminosilicate compositions which are microporous and which are formed from corner sharing $AlO_2$ and $SiO_2$ tetrahedra. By virtually pure silica zeolites is meant that virtually all the aluminum has been removed from the framework. It is well known that it is virtually impossible to remove all the aluminum. Numerically, a zeolite is virtually pure silica when the Si/Al ratio has a value of at least 3,000, preferably 10,000 and most preferably 20,000.

The silica described above can optionally be acid washed (see U.S. patent application Ser. No. 12/701,508 which is incorporated by reference in its entirety) to further improve the properties of the resulting catalyst. Acid washing involves contacting the silica with an acid, including an organic acid or an inorganic acid. Particular inorganic acids include nitric acid, sulfuric acid, and hydrochloric acid, with nitric acid and hydrochloric acid being preferred. The acid concentration in aqueous solution, used for the acid washing, is generally in the range from about 0.05 molar (M) to about 3 M, and often from about 0.1 M to about 1 M. The acid washing can be performed under static conditions (e.g., batch) or flowing conditions (e.g., once-through, recycle, or with a combined flow of make-up and recycle solution).

Representative contacting conditions for acid washing the silica support include a temperature generally from about 20° C. (68° F.) to about 120° C. (248° F.), typically from about 30° C. (86° F.) to about 100° C. (212° F.), and often from about 50° C. (122° F.) to about 90° C. (194° F.). The contacting time is generally from about from about 10 minutes to about 5 hours, and often from about 30 minutes to about 3 hours. It has been determined that acid washing increases the BET surface area of the silica support at least 5% (e.g., from about 5% to about 20%), and often at least 10% (e.g., from about 10% to about 15%). For zeolitic forms of silica, acid washing decreases the amount of aluminum in the framework, i.e. increases the Si/Al ratio. A third effect of acid washing is a decrease in the average pore diameter of the silica support. In general, the pore diameter is decreased by at least about 5%, and often by at least about 10%.

The tungsten-fluoro compound is now grafted onto the desired support by one of several techniques including contacting the support with a solution containing the tungsten-support, sublimation of the tungsten compound onto the support and direct contacting of the tungsten compound with the desired support. When the tungsten compound is contacted with the support using a solution, the compound is first dissolved in an appropriate solvent. Solvents which can be used to dissolve the compound include but are not limited to diethylether, pentane, benzene, and toluene depending on the R groups and compound reactivity. Contacting is carried out at a temperature of about −100° to about 80° C., preferably at a temperature of about −75° to about 35° C. for a time of about 5 minutes to about 24 hours and preferably for a time from about 15 minutes to about 4 hours. The amount of tungsten-fluoro compound dispersed on the support can vary widely but is usually from about 0.5 to about 10 wt % of the catalyst (support plus compound) as the metal. Preferably the amount of compound is from about 1.5 to about 7 wt %.

For sublimation, the tungsten compound is sublimed under dynamic vacuum (typically less than 10-3 torr) onto the support by heating the tungsten compound at a temperature of about 30° to about 150° C. The support is then heated to a temperature of about 30° to about 150° C. for about 1 to 4 hours, and the excess of the tungsten compound is removed by reverse sublimation at a temperature of about 30° to about 150° C. and condensed into a cooled area.

For the direct contact method of grafting the tungsten compound onto the support, the tungsten compound and the support are stirred at a temperature of about −10° to about 100° C. for a time of about 2 to about 6 hours under an inert atmosphere, e.g. argon. All volatile compounds are condensed into another reactor. A solvent such as pentane is then introduced into the reactor by distillation, and the solid is washed three times with the solvent e.g. pentane via filtration—. A condensation cycles. After evaporation of the solvent, the catalyst powder is dried under vacuum. Without being bound by theory, it is thought that regardless of the preparation method, hydroxyls on the support surface react with W—R bond(s) to form W—O-support bonds, with concomitant release of RH. Regardless of the method of preparation or support identity, the catalyst does not comprise a promoter comprising a niobium compound. Promoters are those compounds used in addition to the catalytically active metal to impart high activity at low temperatures. The catalyst of the invention is active at lower temperatures than traditional tungsten oxide olefin metathesis catalysts without the use of a promoter. In an embodiment, the catalyst does not comprise niobium.

The catalyst of the invention is useful as a metathesis catalyst. Olefin metathesis (or disproportionation) processes involve contacting a hydrocarbon feedstock with the catalyst described above at metathesis reaction conditions. The hydrocarbon feedstock refers to the total, combined feed, including any recycle hydrocarbon streams, to the catalyst in the metathesis reactor or reaction zone, but not including any non-hydrocarbon gaseous diluents (e.g., nitrogen), which may be added along with the feed according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in olefin metathesis processes according to the present invention, the hydrocarbons contained in the hydrocarbon feedstock are generally predominantly (i.e., at least 50% by weight, such as from about 60% to about 100% by weight) olefins, typically they comprise at least about 75% (e.g., from about 75% to about 100%) by weight olefins, and often they comprise at least about 85% (e.g., from about 85% to about 100% or from about 95% to about 100%) by weight olefins. In other embodiments, these amounts of olefins are representative of the total olefin percentages in the hydrocarbon feedstock itself, rather than the olefin percentages of the hydrocarbons in the hydrocarbon feedstock. In yet further embodiments, these amounts are representative of the total percentage of two particular olefins in the hydrocarbon feedstock, having differing carbon numbers, which can combine in the metathesis reactor or reaction zone to produce a third olefin having an intermediate carbon number (i.e., having a carbon number intermediate to that of (i) a first olefin (or first olefin reactant) and (ii) a second olefin (or second olefin reactant) having a carbon number of at least two greater than that of the first olefin). In general, the two olefins are present in the hydrocarbon feedstock to the metathesis reactor in a molar ratio of the first olefin to the second olefin from about 0.2:1 to about 10:1, typically from about 0.5:1 to about 3:1, and often from about 1:1 to about 2:1.

In an exemplary embodiment, the two olefins (first and second olefins) of interest are ethylene (having two carbons) and butylene (having four carbons), which combine in the metathesis reactor or reaction zone to produce desired propylene (having three carbons). The term "butylene" is meant to encompass the various isomers of the $C_4$ olefin butene, namely butene-1, cis-butene-2, trans-butene-2, and isobutene. In the case of metathesis reactions involving butylene, it is preferred that the butylene comprises predominantly (i.e., greater than about 50% by weight) butene-2 (both cis and trans isomers) and typically comprises at least about 85% (e.g., from about 85% to about 100%) butene-2, as butene-2 is generally more selectively converted, relative to butene-1 and isobutylene, to the desired product (e.g., propylene) in the metathesis reactor or reaction zone. In some cases, it may be desirable to increase the butene-2 content of butylene, for example to achieve these ranges, by subjecting butylene to isomerization to convert butene-1 and isobutylene, contained in the butylene, to additional butene-2. The isomerization may be performed in a reactor that is separate from the reactor used for olefin metathesis. Alternatively, the isomerization may be performed in an isomerization reaction zone in the same reactor that contains an olefin metathesis reaction zone, for example by incorporating an isomerization catalyst upstream of the olefin metathesis catalyst or even by combining the two catalysts in a single catalyst bed. Suitable catalysts for carrying out the desired isomerization to increase the content of butene-2 in the butylene are known in the art and include, for example, magnesium oxide containing isomerization catalysts as described in U.S. Pat. No. 4,217,244.

As discussed above, the olefins may be derived from petroleum or non-petroleum sources. Crude oil refining operations yielding olefins, and particularly butylene, include hydrocarbon cracking processes carried out in the substantial absence of hydrogen, such as fluid catalytic cracking (FCC) and resid catalytic cracking (RCC). Olefins such as ethylene and butylene are recovered in enriched concentrations from known separations, including fractionation, of the total reactor effluents from these processes. Another significant source of ethylene is steam cracking, as discussed above. A stream enriched in ethylene is generally recovered from an ethylene/ethane splitter as a low boiling fraction, relative to the feed to the splitter, which fractionates at least some of the total effluent from the steam cracker and/or other ethylene containing streams. In the case of olefins derived from non-petroleum sources, both the ethylene and butylene, for example, may be obtained as products of an oxygenate to olefins conversion process, and particularly a methanol to light olefins conversion process. Such processes are known in the art, as discussed above, and optionally include additional conversion steps to increase the butylene yield such as by dimerization of ethylene and/or selective saturation of butadiene, as described in U.S. Pat. No. 7,568,018. According to various embodiments of the invention, therefore, at least a portion of the ethylene in the hydrocarbon feedstock is obtained from a low boiling fraction of an ethylene/ethane splitter and/or at least a portion of the butylene is obtained from an oxygenate to olefins conversion process.

With respect to the first and second olefins (e.g., ethylene and butylene) that undergo metathesis, the conversion level, based on the amount of carbon in these reactants that are converted to the desired product and by-products (e.g., propylene and heavier, $C_5^+$ hydrocarbons), is generally from about 40% to about 80% by weight, and typically from about 50% to about 75% by weight. Significantly higher conversion levels, on a "per pass" basis through the metathesis reactor or reaction zone, are normally difficult to achieve due to equilibrium limitations, with the maximum conversion depending on the specific olefin reactants and their concentrations as well as process conditions (e.g., temperature).

In one or more separations (e.g., fractionation) downstream of the metathesis reactor or reaction zone, the desired product (e.g., propylene) may be recovered in substantially pure form by removing and recovering unconverted olefins (e.g., ethylene and butylene) as well as reaction by-products (e.g., $C_5^+$ hydrocarbons including olefin oligomers and alkylbenzenes). Recycling of the unconverted olefin reactants back to the metathesis reactor or reaction zone may often be desirable for achieving complete or substantially complete overall conversion, or at least significantly higher overall conversion (e.g., from about 80% to about 100% by weight, or from about 95% to about 100% by weight) than the equilibrium-limited per pass conversion levels discussed above. The downstream separation(s) are normally carried out to achieve a high purity of the desired product, particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted feedstock olefin components (e.g., ethylene and propylene) to the desired olefin(s) (e.g., propylene) having an intermediate carbon number is generally at least about 75% (e.g., in the range from about 75% to about 100%) by weight, typically at least about 80% (e.g., in the range from about 80% to about 99%) by weight, and often at least about 90% (e.g., in the range from about 90% to about 97%) by weight, based on the amount of carbon in the converted products. The per pass yield of the desired olefin(s) is the product of the selectivity to this/these product(s) and the per pass conversion, which may be within the ranges discussed above. The overall yield, using separation and recycle of the unconverted olefin reactants as discussed above, can approach this/these product selectivity/selectivities, as essentially complete conversion is obtained (minus some purge and solution losses of feedstock and product(s), as well as losses due to downstream separation inefficiencies).

The conversion and selectivity values discussed above are achieved by contacting the hydrocarbon feedstock described above, either continuously or batchwise, with a catalyst as described herein. Generally, the contacting is performed with the hydrocarbon feedstock being passed continuously through a fixed bed of the catalyst in an olefin metathesis reactor or reaction zone. For example, a swing bed system may be utilized, in which the flowing hydrocarbon feedstock is periodically re-routed to (i) bypass a bed of catalyst that has become spent or deactivated and (ii) subsequently contact a bed of fresh catalyst. A number of other suitable systems for carrying out the hydrocarbon/feedstock contacting are known in the art, with the optimal choice depending on the particular feedstock, rate of catalyst deactivation, and other factors. Such systems include moving bed systems (e.g., countercurrent flow systems, radial flow systems, etc.) and fluidized bed systems, any of which may be integrated with continuous catalyst regeneration, as is known in the art.

Representative conditions for olefin metathesis (i.e., conditions for contacting the hydrocarbon feedstock and catalyst in the olefin metathesis reactor or reaction zone), in which the above conversion and selectivity levels may be obtained, include a temperature from about 75° C. (167° F.) to about 600° C. (1112° F.), and often from about 90° C. (194° F.) to about 500° C. (932° F.), preferably from about 100° C. (212° F.) to about 350° C. (662° F.) and most preferably from about 105° C. (221° F.) to about 250° C. (482° F.); a pressure from about 50 kPa gauge (7.3 psig) to about 8,000 kPa gauge (1160 psig), and often from about 1,500 kPa (218 psig) to about 4,500 kPa (653 psig); and a weight hourly space velocity (WHSV) from about 1 hr$^{-1}$ to about 100 hr$^{-1}$. In an embodiment, the pressure is from about 50 kPa gauge (7.3 psig) to 1310 kPa gauge (190 psig). As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time. Under the olefin metathesis conditions described above, the hydrocarbon feedstock is normally in the vapor phase in the olefin metathesis reactor or reaction zone, but it may also be in the liquid phase, for example, in the case of heavier (higher carbon number) olefin feedstocks.

The following examples are set forth to illustrate the invention. It is to be understood that the examples are only by way of illustration and are not intended as an undue limitation on the broad scope of the invention as set forth in the appended claims.

All experiments were carried out using standard Schlenk and glove-box techniques. Solvents were purified and dried according to standard procedures. SiO$_{2-(700)}$ was prepared from Aerosil™ silica from Degussa (specific area of 200 m$^2$/g), by partial dehydroxylation at 700° C. under high vacuum (10$^{-5}$ Torr) for 15 h to give a white solid having a specific surface area of 190 m$^2$ g$^{-1}$ and containing 0.7 OH nm$^{-2}$.

Example 1

Synthesis of W=OF(CH$_2$CMe$_3$)$_3$

The synthesis of [W=O(CH$_2$CMe$_3$)$_3$F] was carried out according to the following reaction.

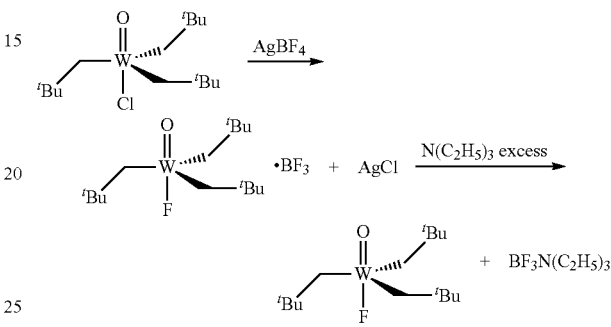

W=O(CH$_2$CH$_2$CMe$_3$))$_3$Cl was synthesized by the literature procedure (Schrock et. al., J. AMER. CHEM. SOC. 1984, 106, 6305-10). [W=O(CH$_2$CMe$_3$)$_3$Cl] (1.5 g) and AgBF$_4$ (0.65 g) were stirred in 20 mL of toluene for one hour at room temperature. The reaction mixture was filtered to remove the insoluble AgCl, and NEt$_3$ (1.1 mL) was added to remove the BF$_3$ moiety by precipitation as BF$_3$.N(C$_2$H$_5$)$_3$. The resulting solution was stirred for 16 h at room temperature and then filtered over celite. The solvent was then removed under vacuum to provide a white solid which was sublimed at 60° C. under reduced pressure (3.10-5 Torr) to yield 1.13 g of product. The product was analyzed and found to contain 41.47% C, 7.89% H and 4.72% F which agrees well with calculated percentages for C$_{15}$H$_{33}$OFW of 41.69% C, 7.69% H and 4.42% F.

Example 2

Synthesis of W(NPh)F(CH$_2$CMe$_3$)$_3$

W(NPh)F(CH$_2$CMe$_3$)$_3$ was synthesized by reaction of WOCl$_4$ with C$_6$H$_5$NCO, followed by alkylation with neopentyl magnesium chloride as shown below.

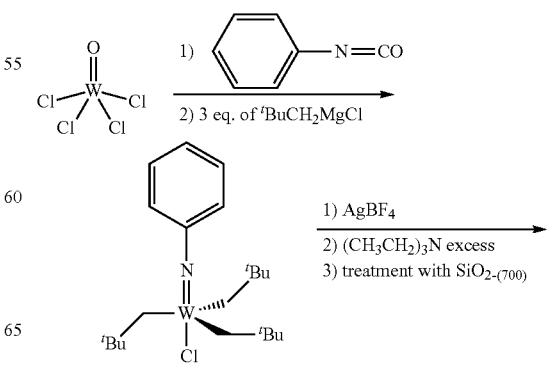

-continued

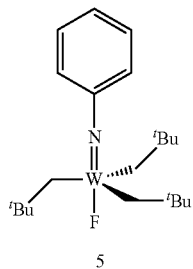

5

Freshly distilled phenylisocyanate (3.214 g) was added to a suspension of [W=OCl$_4$] (9.000 g) in 200 mL of heptane. This mixture was heated at reflux temperature for 4 days to provide a dark brown precipitate. The solvent was removed under vacuum and Et$_2$O (20 mL) was added resulting in a green solution mixture which was filtered to remove the insoluble impurities and Et$_2$O was then removed under vacuum producing a powder of dark green crystals of [W=N(C$_6$H$_5$)Cl$_4$].(Et$_2$O). A solution of 10.6 g [W=N(C$_6$H$_5$)Cl$_4$].(Et$_2$O) in toluene was prepared and stirred rapidly. This solution was cooled to −78° C. and to it there were added (dropwise) 30 mL of a 2.17 M ether solution of neopentylmagnesium chloride. The mixture was warmed up slowly to room temperature with continuous stirring at which point the solvent was removed under vacuum. The resulting product was extracted with pentane, and the extract was treated with activated carbon, stirred for 30 minutes, filtered through a bed of celite, and then the solvent was removed under vacuum. The yellow brown residue was collected on a frit, washed with chilled pentane and dried to give 3.8 g of [W=N(C$_6$H$_5$)(CH$_2$CMe$_3$)$_3$Cl] as a brown powder.

A portion of the [W=N(C$_6$H$_5$)(CH$_2$tBu)$_3$Cl] (2.000 g) obtained above and 0.74 g of AgBF$_4$ were stirred in 20 mL of toluene for one hour at room temperature. The reaction mixture was filtered to remove the insoluble AgCl, and 1.1 mL of NEt$_3$ was added. The resulting solution was stirred for 16 h at room temperature, filtered over celite and the solvent then removed under vacuum to provide a yellow pale solid. The product still contained boron as observed by $^{11}$B NMR. A solution of the product in pentane was added to SiO$_{2\text{-}(700)}$ (500 mg) and reacted for 4 hours. The silica was extracted 3 times with pentane, the solutions combined and the solvent was then removed under vacuum to provide a yellow pale solid. This product was sublimed at 60° C. under reduced pressure (3.10$^{-5}$ Torr) to yield 580 mg of pure product. The product was analyzed and found to contain 48.86% C, 7.38% H, 4.54% F; 2.74% N and 34.90% W which agrees well with calculated percentages for C$_{21}$H$_{38}$FNW of 49.71% C, 7.55% H, 3.74% F; 2.76% N and 36.23% W.

Example 3

Synthesis of WOF(CH$_2$CMe$_3$)$_3$/SiO$_2$

A mixture of the product of Example 1 [WO(CH$_2$CMe$_3$)$_3$F] (500 mg) in pentane (10 mL) and SiO$_{2\text{-}(700)}$ (2 g) was stirred at 25° C. overnight. After filtration, the solid was washed 5 times with pentane and all volatile compounds were condensed into another reactor (of known volume) in order to quantify neopentane evolved during grafting. The resulting white powder was dried under vacuum (10$^{-5}$ Torr). Analysis by gas chromatography indicated the formation of 290 μmol of neopentane during the grafting (1.0±0.1 NpH/W). Elemental analysis showed: W 4.43 wt %; C 3.27 wt %. $^{13}$C NMR showed peaks at 91.5, 34.3, and 31.0 ppm.

Example 4

Synthesis of W(NPh)F(CH$_2$CMe$_3$)$_3$/SiO$_2$

A mixture of the product of Example 2 (500 mg), SiO$_{2\text{-}(700)}$ (2 g) and pentane (10 mL) was stirred at 25° C. overnight. After filtration, the solid was washed 5 times with pentane. The resulting white powder was dried under vacuum (10$^{-5}$ Torr). Elemental analysis: W 4.8 wt %; C 6.5 wt %; N 0.5 wt %.

Comparative Example 5

Synthesis of W(O)Cl(CH$_2$CMe$_3$)$_3$/SiO$_2$

W=O(CH$_2$CH$_2$CMe$_3$))$_3$Cl was synthesized by the literature procedure (Schrock et. al., J. AMER. CHEM. SOC. 1984, 106, 6305-10). This compound was sublimed onto SiO$_{2\text{-}(700)}$ (700 mg) under vacuum. Excess complex was then sublimed away. Elemental analysis showed 4.02 wt % W. $^{13}$C NMR showed peaks at 91.2, 34.2, 31.0 and 24.4 ppm.

Comparative Example 6

Synthesis of W(O)(CH$_2$CMe$_3$)$_4$/SiO$_2$

W=O(CH$_2$CH$_2$CMe$_3$))$_3$Cl was synthesized by the literature procedure (Mazoyer et. al., CHEM. COMMUN. 2010, 46, 8944). This compound was sublimed onto SiO$_{2\text{-}(700)}$ (700 mg) under vacuum. Excess complex was then sublimed away. Elemental analysis showed 4.1 wt % W.

Example 7

Catalytic Testing in Propylene Metathesis of the Catalyst of Example 3

A stainless-steel half-inch cylindrical reactor that can be isolated from ambient atmosphere was charged with 128 mg of the catalyst of Example 3 in a glovebox. After connection to the gas lines and purging of the tubing, a 20 ml/min flow of purified propylene was passed over the catalyst bed at 80° C. Hydrocarbon products were analyzed online by GC. At 30 hours on stream, conversion was 17% and the catalyst exhibited a total turnover number (TON) of 8300. At 100 HOS, TON was 20,000. Selectivity was 50% to ethylene and 50% to 2-butenes. The E/Z ratio of the 2-butene formed was 1.5.

Example 8

Catalytic Testing in Propylene Metathesis of the Catalyst of Example 4

A stainless-steel half-inch cylindrical reactor that can be isolated from ambient atmosphere was charged with 135 mg of the catalyst of Example 4 in a glovebox. After connection to the gas lines and purging of the tubing, a 20 ml/min flow of purified propylene was passed over the catalyst bed at 80° C. Hydrocarbon products were analyzed online by GC. At 30 hours on stream, the catalyst exhibited a total turn over number of 1150. Selectivity was 50% to ethylene and 50% to 2-butenes. The E/Z ratio of the 2-butene formed was 0.9.

Comparative Example 9

Catalytic Testing in Propylene Metathesis of the Catalyst of Example 5

A stainless-steel half-inch cylindrical reactor that can be isolated from ambient atmosphere was charged with 135 mg of the catalyst of Example 5 in a glovebox. After connection to the gas lines and purging of the tubing, a 20 ml/min flow of purified propylene was passed over the catalyst bed at 80° C. Hydrocarbon products were analyzed online by GC. At 30 hours on stream, conversion was 9%. At 100 hours on stream, the catalyst exhibited a total turn over number of 9,000. Selectivity was 50% to ethylene and 50% to 2-butenes. The E/Z ratio of the 2-butene formed was initially less than 1 and stabilized at 1.6.

Example 10

Catalytic Testing in Propylene Metathesis of the Catalyst of Example 6

A stainless-steel half-inch cylindrical reactor that can be isolated from ambient atmosphere was charged with 135 mg of the catalyst of Example 6 in a glovebox. After connection to the gas lines and purging of the tubing, a 20 ml/min flow of purified propylene was passed over the catalyst bed at 80° C. Hydrocarbon products were analyzed online by GC. At 30 hours on stream, conversion was 15%. At 100 hours on stream, the catalyst exhibited a total turnover number of 15,000. Selectivity was 50% to ethylene and 50% to 2-butenes. The E/Z ratio of the 2-butene formed was 1.7.

As can be seen from the results above, using a tungsten metal compound containing at least one tungsten-fluorine bond gives different results than using a tungsten metal compound containing a tungsten-chlorine bond. The catalyst synthesized using a tungsten metal compound containing a tungsten-fluorine bond gives better catalytic results than the catalyst synthesized using a tungsten metal compound containing either a tungsten-chlorine or a tungsten-alkyl bond.

Specific Embodiments

While the following is described in conjunction with specific embodiments, it will be understood that this description is intended to illustrate and not limit the scope of the preceding description and the appended claims.

A first embodiment of the invention is a process comprising contacting a hydrocarbon feedstock with a catalyst that does not comprise a promoter comprising a niobium compound at metathesis conditions to produce an olefin product, wherein the hydrocarbon feedstock comprises olefins including a first olefin and a second olefin having a carbon number of at least two greater than that of the first olefin, to produce a third olefin having an intermediate carbon number and the catalyst comprises a tungsten metal compound characterized in that it contains at least one tungsten-fluorine bond, the compound dispersed on a refractory oxide support wherein the compound is chemically bonded to the support. An embodiment of the invention is one, any or all of prior embodiments in this paragraph up through the first embodiment in this paragraph wherein the tungsten containing compound is selected from the group consisting of $WR_4F$, $WOFR_3$, $W(NR')FR_3$, and mixtures thereof and wherein R is an organic group which does not have any hydrogen atoms beta to the tungsten and R' is an organic group selected from the group consisting of H, phenyl, 2,6-dimethylphenyl and methyl. An embodiment of the invention is one, any or all of prior embodiments in this paragraph up through the first embodiment in this paragraph wherein R is selected from the group consisting of neopentyl ($—CH_2CMe_3$); methyl, 2,2-diethylpropyl ($—CH_2C(CH_2CH_3)_2Me$), and 2,2-diethylbutyl ($—CH_2C(CH_2CH_3)_2CH_2CH_3$). An embodiment of the invention is one, any or all of prior embodiments in this paragraph up through the first embodiment in this paragraph wherein the tungsten is present in an amount from about 0.5 to about 10 wt % of the catalyst as the metal. An embodiment of the invention is one, any or all of prior embodiments in this paragraph up through the first embodiment in this paragraph wherein the refractory oxide support is selected from the group consisting of silica, aluminas, silica-aluminas, titania, zirconia and mixtures thereof. An embodiment of the invention is one, any or all of prior embodiments in this paragraph up through the first embodiment in this paragraph wherein the refractory oxide is silica. An embodiment of the invention is one, any or all of prior embodiments in this paragraph up through the first embodiment in this paragraph wherein the silica is an acid washed silica. An embodiment of the invention is one, any or all of prior embodiments in this paragraph up through the first embodiment in this paragraph wherein the refractory oxide support has a surface area of at least 50 $m^2/g$. An embodiment of the invention is one, any or all of prior embodiments in this paragraph up through the first embodiment in this paragraph wherein the refractory oxide support has a surface area from about 80 to about 500 $m^2/g$. An embodiment of the invention is one, any or all of prior embodiments in this paragraph up through the first embodiment in this paragraph wherein the olefins are present in an amount of at least 80% by weight of the hydrocarbon feedstock. An embodiment of the invention is one, any or all of prior embodiments in this paragraph up through the first embodiment in this paragraph wherein a molar ratio of the first olefin to the second olefin in the hydrocarbon feedstock is from about 0.51 to about 31. An embodiment of the invention is one, any or all of prior embodiments in this paragraph up through the first embodiment in this paragraph wherein the first olefin is ethylene, the second olefin is butylene, and the third olefin is propylene. An embodiment of the invention is one, any or all of prior embodiments in this paragraph up through the first embodiment in this paragraph wherein the hydrocarbon feedstock is contacted with the catalyst at a temperature from about 75° C. (167° F.) to about 400° C. (752° F.), an absolute pressure from about 0.5 bar (7.3 psi) to about 35 bar (508 psi), and a weight hourly space velocity from about 1 to about 100 $hr^{-1}$. An embodiment of the invention is one, any or all of prior embodiments in this paragraph up through the first embodiment in this paragraph wherein a butene feed is isomerized prior to being fed to the catalyst. An embodiment of the invention is one, any or all of prior embodiments in this paragraph up through the first embodiment in this paragraph wherein selectivity to the third olefin is greater than 75%. An embodiment of the invention is one, any or all of prior embodiments in this paragraph up through the first embodiment in this paragraph wherein selectivity to the third olefin is greater than 90%. An embodiment of the invention is one, any or all of prior embodiments in this paragraph up through the first embodiment in this paragraph wherein the selectivity to propylene is at least 90%. An embodiment of the invention is one, any or all of prior embodiments in this paragraph up through the first embodiment in this paragraph wherein the unconverted ethylene and butene are separated from the third olefin propylene and recycled as feed to the process. An embodiment of the invention is one, any or all of prior embodiments in this paragraph up through the first embodiment in this paragraph wherein the hydrocarbon feedstock is contacted with the catalyst at a temperature from about 75° C. (167° F.) to about 400° C. (752° F.), an absolute pressure from about 0.5 bar (7.3 psi) to about 35 bar (508 psi), and a weight hourly space velocity from about 1 to about 100 hr$^{-1}$. An embodiment of the invention is one, any or all of prior embodiments in this paragraph up through the first embodiment in this paragraph wherein at a least a portion of the ethylene in the hydrocarbon feedstock is obtained from a low boiling fraction of an ethylene/ethane splitter and/or at least a portion of the butylene is obtained from an oxygenate to olefins conversion process.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An olefin metathesis process comprising contacting a hydrocarbon feedstock with a catalyst that does not comprise a promoter comprising a niobium compound at metathesis conditions to produce an olefin product, wherein the hydrocarbon feedstock comprises olefins including a first olefin and a second olefin having a carbon number of at least two greater than that of the first olefin, to produce a third olefin having an intermediate carbon number and the catalyst comprises a tungsten metal compound characterized in that it contains at least one tungsten-fluorine bond, the compound dispersed on a refractory oxide support wherein the compound is chemically bonded to the support, wherein the tungsten containing compound is selected from the group consisting of $WR_4F$, $WOFR_3$, $W(NR')FR_3$, and mixtures thereof and wherein R is an organic group which does not have any hydrogen atoms beta to the tungsten and R' is an organic group selected from the group consisting of H, phenyl, 2,6-dimethylphenyl and methyl.

2. The process of claim 1 wherein R is selected from the group consisting of neopentyl (—$CH_2CMe_3$); methyl, 2,2-diethylpropyl (—$CH_2C(CH_2CH_3)_2Me$), and 2,2-diethylbutyl (—$CH_2C(CH_2CH_3)_2CH_2CH_3$).

3. The process of claim 1 wherein the tungsten is present in an amount from about 0.5 to about 10 wt % of the catalyst as the metal.

4. The process of claim 1 wherein the refractory oxide support is selected from the group consisting of silica, aluminas, silica-aluminas, titania, zirconia and mixtures thereof.

5. The process of claim 4 wherein the refractory oxide is silica.

6. The process of claim 5 wherein the silica is an acid washed silica.

7. The process of claim 1 wherein the refractory oxide support has a surface area of at least 50 m$^2$/g.

8. The process of claim 7 wherein the refractory oxide support has a surface area from about 80 to about 500 m$^2$/g.

9. The process of claim 1 wherein the olefins are present in an amount of at least 80% by weight of the hydrocarbon feedstock.

10. The process of claim 1 wherein a molar ratio of the first olefin to the second olefin in the hydrocarbon feedstock is from about 0.5:1 to about 3:1.

11. The process of claim 1 wherein the first olefin is ethylene, the second olefin is butylene, and the third olefin is propylene.

12. The process of claim 1 wherein the hydrocarbon feedstock is contacted with the catalyst at a temperature from about 75° C. (167° F.) to about 400° C. (752° F.), an absolute pressure from about 0.5 bar (7.3 psi) to about 35 bar (508 psi), and a weight hourly space velocity from about 1 to about 100 hr$^{-1}$.

13. The process of claim 11 wherein a butene feed is isomerized prior to being fed to the catalyst.

14. The process of claim 1 wherein selectivity to the third olefin is greater than 75%.

15. The process of claim 1 wherein selectivity to the third olefin is greater than 90%.

16. The process of claim 11 wherein the selectivity to propylene is at least 90%.

17. The process of claim 11 wherein the unconverted ethylene and butene are separated from the third olefin propylene and recycled as feed to the process.

18. The process of claim 11 wherein the hydrocarbon feedstock is contacted with the catalyst at a temperature from about 75° C. (167° F.) to about 400° C. (752° F.), an absolute pressure from about 0.5 bar (7.3 psi) to about 35 bar (508 psi), and a weight hourly space velocity from about 1 to about 100 hr$^{-1}$.

19. The process of claim 11 wherein at a least a portion of the ethylene in the hydrocarbon feedstock is obtained from a low boiling fraction of an ethylene/ethane splitter and/or at least a portion of the butylene is obtained from an oxygenate to olefins conversion process.

* * * * *